US006355847B1

(12) United States Patent
Tsuruya

(10) Patent No.: US 6,355,847 B1
(45) Date of Patent: Mar. 12, 2002

(54) METHOD OF MANUFACTURING PHENOL BY DIRECT OXIDATION OF BENZENE

(75) Inventor: Shigeru Tsuruya, Kobe (JP)

(73) Assignee: President of Kobe University, Kobe (JP)

( * ) Notice: Subject to any disclaimer, the term of this patent is extended or adjusted under 35 U.S.C. 154(b) by 0 days.

(21) Appl. No.: 09/362,717

(22) Filed: Jul. 29, 1999

(30) Foreign Application Priority Data

Jan. 27, 1999 (JP) .......................................... 11-018084

(51) Int. Cl.⁷ .............................................. C07C 37/58
(52) U.S. Cl. .................................................... 568/802
(58) Field of Search ........................................ 568/802

(56) References Cited

U.S. PATENT DOCUMENTS

| | | | | | |
|---|---|---|---|---|---|
| 3,804,906 A | * | 4/1974 | McAvoy | ...................... | 568/802 |
| 5,426,245 A | * | 6/1995 | Hamada | ...................... | 568/802 |
| 5,912,391 A | * | 6/1999 | Barnhart | ...................... | 568/802 |
| 5,962,752 A | * | 10/1999 | Durante | ...................... | 568/802 |

FOREIGN PATENT DOCUMENTS

| DE | 196 34 406 | 3/1998 |
|---|---|---|
| WO | WO 98/15514 | 4/1998 |

OTHER PUBLICATIONS

T. Ohtani, et al., "Liquid–Phase Oxidation of Benzene with Molecular Oxygen Catalyzed by Cu–Zeolites," PROCEEDINGS OF THE 10$^{TH}$ INTERNATIONAL CONGRESS ON CATALYSIS, Jul. 19–24, 1992, Budapest Hungary, pp. 1999–2002.

"Liquid–Phase Benzene Oxidation to Phenol with Molecular Oxygen Catalyzed by Cu–Zeolites," JOURNAL OF CATALYSIS 155, 1995, pp. 158–162.

Junji Okamura, et al., "Formation of Cu–Supported Mesoporous Silicates and Aluminosilicates and Liquid–Phase Oxidation of Benzene Catalyzed by the Cu–Mesoporous Silicates and Aluminosilicates," JOURNAL OF MOLECULAR CATALYSIS A: CHEMICAL 135, 1998, pp. 133–142.

Miyake, Applied Catatlysis A: General, vol. 131, pp. 33–42, 1995.*

* cited by examiner

*Primary Examiner*—Michael L. Shippen
(74) *Attorney, Agent, or Firm*—Oblon, Spivak, McClelland, Maier & Neustadt, P.C.

(57) ABSTRACT

Benzene, ascorbic acid acting as a reducing agent, and a vanadium-supported alumina catalyst are placed in an aqueous solution of acetic acid used as a solvent, and the reaction is carried out under an oxygen gas atmosphere having a pressure of at least 0.3 MPa so as to directly oxidize benzene and, thus, to obtain phenol at a high yield of at least 8%.

11 Claims, 1 Drawing Sheet

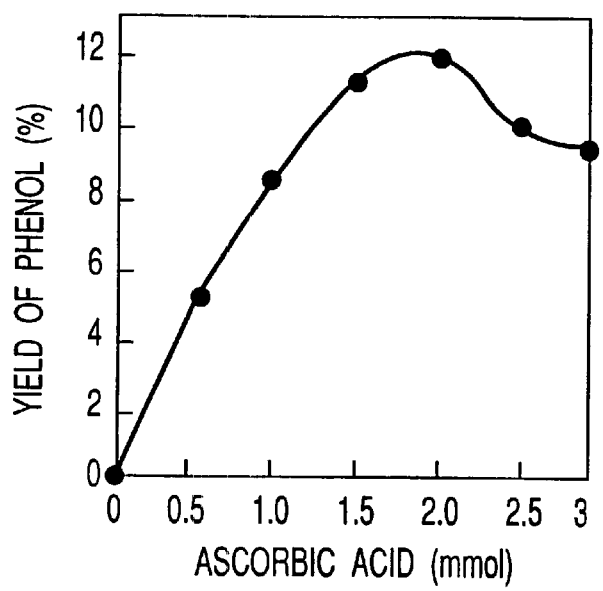
F I G. 1
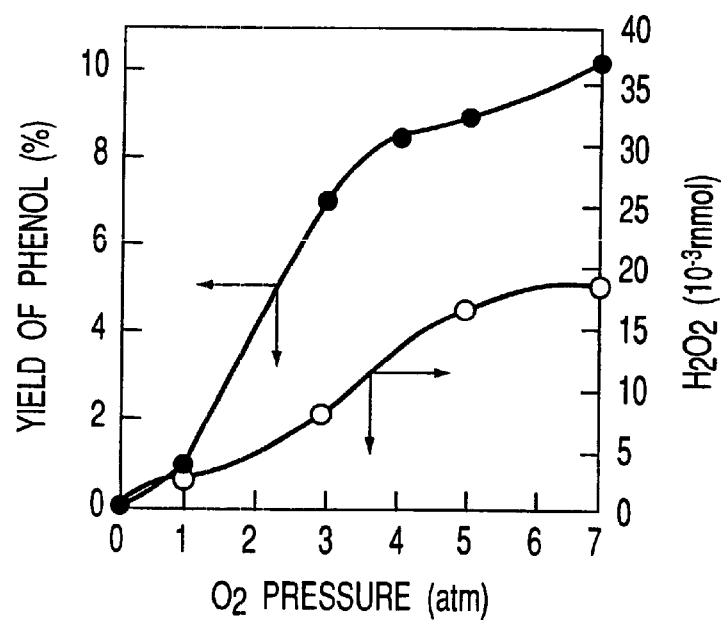
F I G. 2

METHOD OF MANUFACTURING PHENOL BY DIRECT OXIDATION OF BENZENE

BACKGROUND OF THE INVENTION

The present invention relates to a method of manufacturing phenol by a single stage direct oxidation of benzene.

A cumene process is widely used for manufacturing phenol. In the cumene process, phenol is obtained from the starting material benzene by the steps (I) to (III) given below:

(I) Cumene is produced by the reaction between benzene and propylene in the presence of an acid catalyst.

(II) Cumene hydroperoxide is produced by the reaction between cumene and oxygen.

(III) Cumene hydroperoxide is decomposed in the presence of an acid catalyst into phenol and acetone.

However, the cumene process, which involves three process steps, is not economical. Also, the phenol manufacture is dependent on the market price of acetone obtained as a by-product in the cumene process.

Under the circumstances, the present inventor has conducted an extensive research on the method to obtain phenol by direct oxidation of benzene in the presence of a Cu-supported catalyst. However, the conventional method is not satisfactory in the phenol yield and leaves room for further improvement in the phenol manufacturing cost.

BRIEF SUMMARY OF THE INVENTION

An object of the present invention is to provide a method of manufacturing phenol by direct oxidation of benzene.

According to a first aspect of the present invention, there is provided a method of manufacturing phenol, comprising the steps of placing benzene, a reducing agent and a vanadium-supported alumina catalyst in an aqueous solution of acetic acid used as a solvent, and directly oxidizing benzene under an oxygen gas atmosphere to produce phenol.

According to a second aspect of the present invention, there is provided a method of manufacturing phenol, comprising the steps of placing benzene and a zinc-vanadium-supported alumina catalyst in an aqueous solution of acetic acid used as a solvent, and directly oxidizing benzene under an oxygen gas atmosphere to produce phenol.

Further, according to a third aspect of the present invention, there is provided a method of manufacturing phenol, comprising the steps of supplying benzene and an oxidant of $N_2O$ into a circulating reactor loaded with a copper-supported zeolite catalyst, and directly oxidizing benzene to produce phenol.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a graph showing the relationship between the amount of ascorbic acid and the phenol yield in the reaction in Example 1 of the present invention; and FIG. 2 is a graph showing the relationship among the oxygen pressure, the phenol yield and the formation of $H_2O_2$ in the reaction in Example 1 of the present invention.

DETAILED DESCRIPTION OF THE INVENTION

The present invention provides a method of manufacturing phenol by direct oxidation of benzene by a liquid phase catalytic process or a gas phase catalytic process.

In the method according to the first aspect of the present invention, phenol is obtained by direct oxidation of benzene using a reducing agent, e.g., ascorbic acid. The candidate compounds used as a reducing agent include, for example, hydroquinone, pyrocatechol, sodium sulfite and zinc in addition to ascorbic acid. A vanadium-supported alumina catalyst. ($V/Al_2O_3$ catalyst) is used for the direct oxidation of benzene for producing phenol. An ion exchange method, an impregnation method, a sol-gel method, etc., can be employed for having vanadium supported by alumina. An aqueous solution of acetic acid having a concentration of about 1N is used as a solvent. A molar ratio of benzene to the reducing agent such as ascorbic acid should desirably be set to fall within a range of between 1:0.15 to 1:0.5. The reaction is carried out under an atmosphere of an oxygen gas acting as an oxidant, the oxygen gas atmosphere having a pressure of, for example, 1 to 10 atm (about 0.1 to 1 MPa), preferably 3 to 10 atm (about 0.3 to 1 MPa). The reaction temperature should desirably be set at 293 to 333K and the reaction time should desirably be set at 10 to 25 hours. Alumina is used as a support of the vanadium catalyst in the method of the present invention because the amount of the vanadium elution during the reaction can be diminished, compared with the use of another support such as silica or MCM-41.

In the method according to the first aspect of the present invention, phenol is considered to be produced by direct oxidation of benzene through reactions (1) to (5) given below, which involves hydrogen peroxide formation. Under the optimum conditions given above, phenol can be obtained at a high yield, i.e., at least 8%.

$V^{5+}$+ascorbic acid+½$O_2$→$V^{4+}$+dehydroascorbic acid+$H_2O$    (1)

$2V^{4+}+O_2+2H^+→2V^{5+}+H_2O_2$    (2)

$V^{4+}+H_2O_2+H^+→V^{5+}+·OH+H_2O$    (3)

(4)

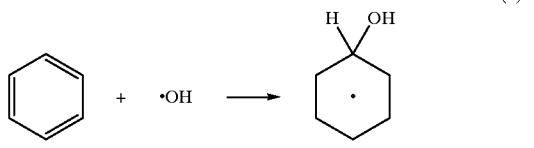

(5)

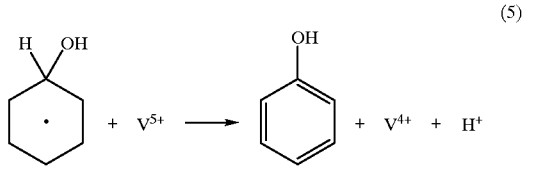

In the method according to the second aspect of the present invention, phenol is manufactured by direct oxidation of benzene using a zinc-vanadium-supported alumina catalyst ($Zn—V/Al_2O_3$ catalyst). in place of the $V/Al_2O_3$ catalyst used in the method of the first aspect.

Zinc contained in the $Zn—V/Al_2O_3$ catalyst exhibits a reducing function and, thus, ascorbic acid used as a reducing agent in the method of the first aspect is not used in the method of the second aspect. The other conditions are equal to those for the method of the first aspect.

The phenol yield is not high in the method of the second aspect. However, since a costly reducing agent such as ascorbic acid is not used, it may be possible to lower the manufacturing cost of phenol.

In the method of manufacturing phenol by direct oxidation of benzene according to the third aspect of the present invention, a gas phase catalytic reaction is employed in place of the liquid phase catalytic reaction employed in the method of each of the first and second aspects. In the method of the third aspect, benzene and $N_2O$ used as an oxidant are supplied into a continuous flow reactor loaded with a copper-supported zeolite catalyst. A carrier gas, e.g., nitrogen gas, is used for supplying benzene and $N_2O$ gas into the reactor. The reaction pressure should desirably be set at 1 atm (about 0.1 MPa) or more, and the reaction temperature should desirably be set to fall within a range of 650 to 700K.

In the method of the third aspect in which $N_2O$ is used as an oxidant, phenol can be obtained at a high yield, compared with the case where $O_2$ is used as an oxidant.

EXAMPLES

Example 1

An alumina support was impregnated with an ethanol solution of $VO(C_5H_7O_2)_2$, followed by drying the alumina support for 24 hours. Then, the alumina support was baked at 573K for 3 hours under an air stream to prepare a vanadium-supported alumina catalyst, the catalyst containing 2% by weight of vanadium.

Loaded in a batch type reactor were 0.1 g of the $V/Al_2O_3$ catalyst prepared as above, 5.6 mmol of benzene, 5 mL of 1N (80% by volume) aqueous solution of acetic acid used as a solvent, and ascorbic acid used as a reducing agent. Reaction was carried out within the reactor for 24 hours at 333K under an oxygen atmosphere while stirring the reaction system with a magnetic stirrer. The reaction product was analyzed by a gas chromatography.

The relationship between the amount of ascorbic acid and the phenol yield was examined. Specifically, the pressure of the oxygen atmosphere was set at 4 atm (about 0.4 MPa), and the amount of ascorbic acid was changed within a range of 0 to 3 mmol. FIG. 1 shows the results. As apparent from FIG. 1, phenol was obtained at a high yield of 8% or more where the amount of ascorbic acid was at least 1 mmol.

Incidentally, under the conditions that permitted the phenol yield to have reached a maximum value of about 12% as shown in FIG. 1, the amount of vanadium elution from the $V/Al_2O_3$ catalyst was found to be about 40%.

Then, the relationship among the oxygen pressure, the phenol yield and the $H_2O_2$ formation was examined. Specifically, the amount of ascorbic acid was set at 1 mmol, and the pressure of the oxygen atmosphere was changed within a range of 0 to 7 atm (0 to about 0.7 MPa). FIG. 2 shows the results. As apparent from FIG. 2, phenol can be obtained at a high yield of 7% or more, if the oxygen pressure is at least 3 atm.

Example 2

A zinc-vanadium-supported alumina catalyst (Zn—V/$Al_2O_3$ catalyst) was prepared by impregnating an alumina support with vanadium and zinc exhibiting a reducing function. Then, phenol was produced under the conditions equal to those in Example 1, except that the Zn—V/$Al_2O_3$ catalyst was used in place of the V/$Al_2O_3$ catalyst and that the reducing agent of ascorbic acid was not used. Phenol was obtained with a yield of 0.1%.

As described above, in the case of using Zn—V/$Al_2O_3$ catalyst, phenol can be obtained without using ascorbic acid that is costly, though the phenol yield is low. Therefore, it is possible to manufacture phenol at a low manufacturing cost.

Example 3

Prepared was a copper ion-exchanged H type ZSM-5 zeolite catalyst (Cu/HZSM-5 catalyst) containing 1% by weight of copper. The Cu/HZSM-5 catalyst was loaded in a fixed bed continuous flow type reactor, and a mixed gas consisting of a $N_2O$ gas (oxidant), a $N_2$ gas (carrier gas) and benzene, which were mixed at a molar ratio of 11:10:1, was supplied into the reactor. The mixed gas was supplied at a ratio W/F, where W denotes the catalyst weight (g-cat.) and F denotes the mixed gas flow rate (mol/min), of $4.2 \times 10^2$ (g-cat.mol/min), and the reaction was carried out under the pressure of 1 atm and the temperature of 673K. The initial yield of phenol was found to be 6.3%.

An additional experiment was conducted under substantially the same conditions, except that $O_2$ gas was used as the oxidant in place of the $N_2O$ gas. In this case, the initial yield of phenol was found to be 0.8%.

As apparent from the experimental data, where phenol is produced by direct oxidation of benzene by a gas phase catalytic reaction, the phenol yield in the case of using $N_2O$ as an oxidant is higher than that in the case of using $O_2$ as an oxidant.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing phenol, comprising the steps of:
   placing benzene, a reducing agent and a zinc-vanadium-supported on alumina catalyst in an aqueous solution of acetic acid used as a solvent; and
   directly oxidizing benzene under an oxygen gas atmosphere to produce phenol.

2. The method according to claim 1, wherein the pressure of the oxygen gas atmosphere is 0.1 to 1 MPa.

3. The method according to claim 2, wherein the pressure of the oxygen gas atmosphere is 0.3 to 1 MPa.

4. The method according to claim 1, wherein the reaction temperature is 293 to 333K.

5. The method according to claim 1, wherein the reaction time is 10 to 25 hours.

6. A method of manufacturing phenol, comprising the steps of:
   placing benzene, a reducing agent and a vanadium-supported on alumina catalyst in an aqueous solution of acetic acid used as a solvent, the reducing agent being selected from the group consisting of ascorbic acid, hydroquinone, pyrocatechol, sodium sulfite and zinc; and directly oxidizing benzene under an oxygen gas atmosphere to produce phenol.

7. The method according to claim 6, wherein the molar ratio of benzene to the reducing agent falls within the range of 1:0.15 to 1:0.5.

8. The method according to claim 6, wherein the pressure of the oxygen gas atmosphere is 0.1 to 1 Mpa.

9. The method according to claim 8, wherein the pressure of the oxygen gas atmosphere is 0.3 to 1 Mpa.

10. The method according to claim 6, wherein the reaction temperature is 293 to 333° K.

11. The method according to claim 6, wherein the reaction time is 10 to 25 hours.

* * * * *